(12) United States Patent
Besch et al.

(10) Patent No.: US 9,597,491 B2
(45) Date of Patent: Mar. 21, 2017

(54) DEVICE FOR THE SEALING CONNECTION OF A PRESSURE HOSE WITH A GRIP ELEMENT OR WITH A CONNECTOR OF A SURGICAL INSTRUMENT

(75) Inventors: Hansjoerg Besch, Gomaringen (DE); Markus Amann, Tuebingen (DE); Christian Sick, Nehren (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 781 days.

(21) Appl. No.: 13/211,895

(22) Filed: Aug. 17, 2011

(65) Prior Publication Data

US 2012/0046654 A1  Feb. 23, 2012

(30) Foreign Application Priority Data

Aug. 18, 2010 (DE) .......................... 10 2010 037 027

(51) Int. Cl.
*A61B 18/02* (2006.01)
*A61M 39/12* (2006.01)
*A61M 39/10* (2006.01)

(52) U.S. Cl.
CPC ............. *A61M 39/12* (2013.01); *A61B 18/02* (2013.01); *A61B 2018/0262* (2013.01); *A61M 39/1011* (2013.01); *Y10T 16/466* (2015.01)

(58) Field of Classification Search
CPC ............... A61B 2017/0046–2017/0047; A61B 1/00128; A61B 2018/0091; A61B 2018/0172; A61B 2018/0231; A61B 18/02; A61B 2018/0262; F16L 27/11; F16L 251/028; A61M 39/10; A61M 39/12

USPC ............................... 606/20–26, 41–529, 1–3
See application file for complete search history.

(56) References Cited

U.S. PATENT DOCUMENTS

| | | | | |
|---|---|---|---|---|
| 2,956,586 | A | * | 10/1960 | Zeigler et al. ................ 137/563 |
| 4,431,216 | A | | 2/1984 | Legris |
| 4,712,813 | A | * | 12/1987 | Passerell et al. ............. 285/250 |
| 5,174,611 | A | * | 12/1992 | Byrd et al. ...................... 285/45 |
| 5,511,830 | A | * | 4/1996 | Olson et al. .................. 285/243 |
| 5,853,204 | A | * | 12/1998 | Bartholomew ............... 285/305 |
| 6,814,726 | B1 | | 11/2004 | Lauer |

(Continued)

FOREIGN PATENT DOCUMENTS

| CN | 2822543 Y | 10/2006 |
|---|---|---|
| CN | 101188977 A | 5/2008 |

(Continued)

*Primary Examiner* — Jocelyn D Ram
(74) *Attorney, Agent, or Firm* — Blank Rome LLP

(57) ABSTRACT

A device for the sealing connection of a pressure hose with a grip element of a surgical instrument. The device comprising at least one sealing element that, in an assembled state, is interposed between the grip element and the pressure hose in a connecting region to create a seal. A support element is provided and arranged in the connecting region in the interior of the pressure hose such that the sealing element is clamped, or can be clamped, between the support element and the pressure hose on one side and the grip element on the other side. In addition, a handle for a surgical device, in particular a cryogenic surgical instrument, comprising a grip element for holding the surgical instrument and comprising at least one pressure hose that is connected, or can be connected, with the grip element via the device for the sealing connection.

19 Claims, 2 Drawing Sheets

(56) References Cited

U.S. PATENT DOCUMENTS

| | | | |
|---|---|---|---|
| 7,125,052 B2* | 10/2006 | Robison et al. | 285/256 |
| 7,189,228 B2* | 3/2007 | Eum et al. | 606/22 |
| 2002/0022832 A1* | 2/2002 | Mikus et al. | 606/20 |
| 2003/0006610 A1 | 1/2003 | Werth | |
| 2003/0028182 A1 | 2/2003 | Abboud et al. | |
| 2004/0227346 A1* | 11/2004 | Jamison et al. | 285/381.3 |
| 2005/0095891 A1* | 5/2005 | Schorn | 439/274 |
| 2008/0214990 A1* | 9/2008 | Smutney et al. | 604/27 |
| 2009/0138010 A1 | 5/2009 | DeCarlo | |
| 2009/0163902 A1 | 6/2009 | DeLonzor et al. | |
| 2012/0046655 A1* | 2/2012 | Besch et al. | 606/20 |
| 2013/0035678 A1* | 2/2013 | Sick et al. | 606/20 |

FOREIGN PATENT DOCUMENTS

| | | |
|---|---|---|
| DE | 201 09 980 U1 | 11/2002 |
| FR | 2 562 984 A1 | 10/1985 |

* cited by examiner

DEVICE FOR THE SEALING CONNECTION OF A PRESSURE HOSE WITH A GRIP ELEMENT OR WITH A CONNECTOR OF A SURGICAL INSTRUMENT

FIELD OF THE INVENTION

Embodiments of the invention relate to a device for the sealing connection of a pressure hose with a grip element or with a connector of a surgical instrument, said device comprising at least one sealing element that, in an assembled state, is interposed between the grip element and the pressure hose so as to provide a seal in a connecting region. In addition, embodiments of the invention relate to a handle for a surgical instrument, in particular a cryogenic surgical instrument, comprising a grip element for holding the surgical instrument and comprising at least one pressure hose, the grip element of said hose being connected or connectable by way of the aforementioned device.

BACKGROUND

Such connecting devices and handles comprising connecting devices of this type have been known from the prior art. They are used in apparatus-assisted surgery and, in particular, in cryosurgery or water jet surgery, wherein operations on human and animal tissue are possible with the use of an appropriately equipped surgical instrument. Considering such surgical instruments, it is necessary in most cases that an application fluid, or a similarly acting fluid, be delivered to a grip element via a pressure hose, and then fed by way of said grip element to an application head such as for example, an application nozzle or a cryogenic probe.

Due to the sterility requirements that are applicable to such surgical instruments, the connecting device used for connecting the pressure hose(s) with the grip element is subject to strict requirements. Referring, in particular, to such grip instruments that, after use, are placed in an automatic washer for machine washing, for example, it is highly necessary that the connecting device be configured such that a lasting seal and an inexpensive connection between the pressure hose and the grip element, or a connector provided on said grip element, be ensured.

Prior art has disclosed connecting devices or handles for surgical instruments, in which the pressure hose is connected, via a screw connection, with the grip element. To accomplish this, an O-ring or a similar sealing element is compressed in an axial direction, creating a radially sealing connection fastening the hose to the grip element in a sealing manner. Because of the screw connection, the pressure hose is additionally compressed such that an axial tensile load acting on the hose can be removed.

There is a problem that a solution-resistant connection cannot be ensured beyond the desired number of processing operations due to the setting and flow behavior of the plastic pressure hose. In addition, it is sometimes possible for deformations to occur due to the axial compression of the O-ring caused by the high compressive forces; the deformations being above the permissible range, leading to premature failure or to an irreversible deformation of the sealing element.

SUMMARY

Consequently, it is the object of the embodiments of the invention to provide a device for the sealing connection of a pressure hose with a grip element of a surgical instrument or with a handle for such a surgical instrument, said connection ensuring a lasting, tight connection of the pressure hose with the grip element.

In particular, it is necessary that the connection between the pressure hose and the grip element withstand an operating pressure between approximately 40 bar and 65 bar (safety limit being 130 bar) and, in addition, be absolutely fluid-tight and gas-tight. Likewise, the sealing elements that are being used must be able to withstand at least 100 processing cycles at 138° C. (i. e., washing and sterilization).

It is noted that this also means the connection of the pressure hose with a connector, which, in this case, acts as the coupling element with a fluid source or a consumer in a surgical application.

In particular, the aforementioned objects are achieved with a device for the sealing connection of a pressure hose with a grip element of a surgical instrument or with a connector, said device comprising at least one sealing element that, in an assembled state, is arranged, or can be arranged, in a connecting region so as to create a seal between the grip element (or connector) and the pressure hose. A support element is arranged in the connecting region on the inside of the pressure hose such that the sealing element is clamped, or can be clamped, between the support element and the pressure hose on one side and the grip element on the other side.

In addition, the aforementioned objects are achieved with a handle for a surgical instrument, in particular a cryogenic surgical instrument, said handle comprising a grip element for holding the surgical element and at least one pressure hose that is connected, or can be connected, with the grip element via a device described above.

Consequently, the arrangement of a support element in the connecting region is an essential aspect such that said support element acts from the inside of the pressure hose in an outward direction on the sealing element such that the sealing element is clamped, or can be clamped, between the support element and the pressure hose on one side and the grip element on the other side. Considering such an embodiment, the sealing element is preferably subject to the application of a load and is preferably deformed perpendicularly to the axial direction of the pressure hose in the connecting region; considering the device in accordance with the embodiments of the invention, this direction of the application of the load decidedly contributes to the lasting sealing effect, even under the aforementioned thermal stresses. Preferably, the sealing element is pressed in a radial direction.

Considering the stress in which the sealing element is subjected radially to the axis of the pressure hose, the support element decidedly prevents a deformation of the pressure hose at the contact point of the sealing element so that the sealing effect is decidedly improved.

In doing so, the sealing element is preferably supported in a sealing element receptacle on the grip element and, in particular, in a manner that the combination of the support element and the pressure hose can be inserted into the grip element such that the sealing element abuts against said grip element in a sealing manner, tightly sealing the transition region between the pressure hose and the grip element.

It should be recognized that it is also possible to bring the sealing element in operative connection with the pressure hose even before the pressure hose is inserted into the grip element and to then insert the assembly comprising the sealing element, the support element and the pressure hose into the grip element in a sealing manner.

Preferably, the sealing element comprises at least one O-ring, or a similar enveloping element, circumscribing the pressure hose and the support element in an assembled state; in which case the assembled state is defined as the state in which the pressure hose is connected with the grip element in a sealing manner.

Preferably, the sealing element comprises an O-ring, or a similar enveloping element, circumscribing the pressure hose and the support element, said enveloping element—in an assembled state—being slipped or being capable of being slipped onto the pressure hose such that said enveloping element sealingly abuts against said pressure hose to create a seal and form a sealing transition between the pressure hose and the grip element, in combination with the grip element and, in particular, with an inside wall of a receiving region of the grip element.

Also, in this situation, it is possible to arrange the O-ring or enveloping element in the grip element and, in particular, in a sealing element receptacle on the grip element, and to subsequently insert the pressure hose together with the support element into the O-ring so as to form a sealing connection, or to already slip the O-ring over the support element and the pressure hose, and to subsequently insert the combination of the support element, pressure hose and O-ring into the grip element into a receiving region that has a suitable recess such as, for example, a sealing element receptacle. Hereinafter, the term "O-ring" shall also include the possibility of using the enveloping element.

Preferably, the sealing element comprises at least two O-rings, or similar enveloping elements, circumscribing the pressure hose and the support element, these O-rings being uncoupled from each other via at least one spacer element. The uncoupling of the two O-rings using the spacer element constitutes an additional improvement of the sealing effect.

Preferably, the spacer element is supported, or can be supported, as a stand-alone component in a spacer element receptacle on the grip element, in particular in an axial direction of the enveloping tube in the connecting region between the two O-rings (or similar enveloping elements). As has already been previously mentioned with reference to the O-rings, it is also possible to insert the spacer element in a spacer element receptacle on the grip element before inserting the pressure hose in the grip element and to align said spacer element with the two O-rings, in particular, or also to slip the spacer element and at least one O-ring onto the pressure hose before insertion.

Preferably, the spacer element is configured as a ring or bushing that can be slipped on the pressure hose. The dimensions of the spacer element, e.g., a spacer element configured as a spacer ring or spacer bushing, are selected such that they are—with reference to the outside diameter—slightly smaller that the sealing element(s), so that the sealing elements can deform while optimizing the sealing effect without such a deformation being hindered by the spacer element.

Preferably, the support element is configured as a support bushing that has an outside diameter that is complementary to the inside diameter of the enveloping tube and is, in particular, slightly larger so that the support element in the interior of the enveloping tube expands said outside diameter. In this manner, the support element is firmly placed in the interior of the pressure hose, so that the insertion of the pressure hose into the receiving region of the grip element and the slipping into the O-rings or enveloping elements can be safely done.

Preferably, the axis of rotation of the O-rings is arranged such that said axis of rotation is parallel to the axis of the pressure hose and parallel to the axis of a potentially present spacer element. In this manner, the support element and the pressure hose can be axially inserted in the O-rings, or the enveloping element, so that a tight connection with the grip element is achieved in the assembled state.

Preferably, at least one holding element is arranged, or can be arranged, on the pressure hose, said holding element being, or being capable of being, in operative connection with an abutment element on the grip element to hold in place the pressure hose in an axial direction of the pressure hose in the connecting region. Such an arrangement ensures the safe fixation of the pressure hose in the grip element.

Preferably, the holding element comprises a crimp ring, or a similar fixation element, that is arranged, or can be arranged, in a stationary manner on the outside of the pressure hose. Such a crimp ring (or similar fixation element) can thus be slipped, for example, onto the outside of the pressure hose and crimped or otherwise fixed in place there. Regarding this, it is possible to use any method for arranging a holding element on a pressure hose as is known in the art.

Preferably, the crimp ring (or similar fixation element) has at least one fixation extension that, in the assembled state, projects from the outside of the pressure hose in the direction of the interior of the pressure hose. The assembled state, of course, is meant to refer to the state in which the crimp ring (or similar fixation element) is arranged on the pressure hose. By providing a fixation extension of the aforementioned type, the removal of forces by the crimp ring (or similar fixation element) is improved so that even extremely great forces and, in particular, forces acting on the pressure hose in the axial direction, can be removed from the holding element.

Preferably, the abutment element comprises at least one fastening means that can be used to bring said abutment element into a specifically releasable locking or supporting engagement with the grip element and/or with the holding element. Consequently, the abutment element may, for example, be a locking ring that is slipped, or can be slipped, over the pressure hose and that, following the insertion of the pressure hose in combination with the holding element arranged thereon, can be secured on the grip element such that it holds the holding element in place and can be brought into engagement with the grip element such that it fixes the holding element in place and, in particular, supports it against being pulled out of the grip element in instances of application of an axial tensile load on the pressure hose. Thus, the abutment element may be provided as a locking ring that can be brought into engagement with the grip element. It should be appreciated that it is also possible to configure the abutment element as a bayonet joint element that can be locked together with the grip element via a bayonet joint and, in doing so, deflects forces into the grip element, said forces having been introduced through the holding element. Any prior art devices for fixation of the abutment element against the grip element or for locking or supporting the holding element on the abutment element can be used in this situation.

Preferably, an insertion element is arranged on the free distal end of the pressure hose and/or the support element, i.e., on the end that is used to insert the pressure hose or the support element into the grip element and, in particular, into the O-rings or similar enveloping elements, said insertion element being configured such that it assists the insertion of the pressure hose together with the support element into the receiving region of the grip element, in particular, in the interior of the O-ring or similar enveloping element or a potentially provided spacer element. Such an insertion element may, for example, be an appropriately chamfered distal end of the pressure hose and/or the support element so that the resultant guide surfaces facilitate the insertion of the pressure hose together with the support element.

As has already been mentioned above, embodiments of the invention also relate to a handle for a surgical instrument, in particular a cryosurgical instrument, comprising a grip element for holding the surgical instrument and comprising at least one pressure hose that is connected, or can be connected, with a grip element using a device in accordance with the aforementioned embodiments. To avoid being redundant, additional explanations regarding the embodiment of this device are omitted and explicit reference is made to the previous passages.

Additional embodiments of the invention can be inferred from the dependent claims.

BRIEF DESCRIPTION OF THE DRAWINGS

Embodiments of the invention will be described in greater detail with reference to the drawings, in which.

DETAILED DESCRIPTION

Hereinafter, the same reference numbers are used for the same parts and parts acting in the same manner, whereby, in some instances, a prime is used also.

Figure 1:
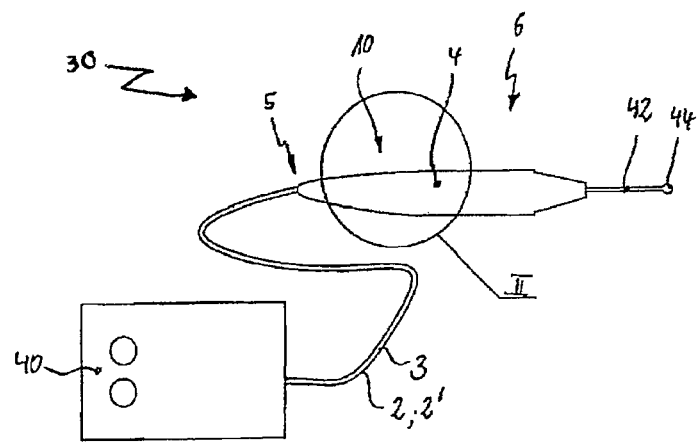
FIG. 1 is a schematic representation of an embodiment of a surgical instrument.

FIG. 1 shows an embodiment of a surgical instrument 30 such as is used, for example, in cryosurgery or water jet surgery.

Shown is a delivery unit 40 that supplies a handle 6 with an application fluid via a tubing set 3. In doing so, the tubing set 3 comprises two pressure hoses 2, 2', one of which being used as a feed hose, the other being used as a discharge hose, in order to feed application fluid from the supply unit 40 to the handle 6 and to discharge said fluid therefrom.

The handle 6, in turn, comprises a grip element 4 that is disposed to accommodate the tubing set 3 or the pressure hoses 2, 2' and an application probe 42, said probe 42 being configured as, for example, a cryosurgical probe with a coaxial conduit. This means that the application fluid supplied via the supply unit 40 is transported through a pressure hose 2 into the grip element 4 and from there, via an appropriate pressure hose guide, into the application probe 42. There, the application fluid is transported in an exterior coaxial conduit, i.e., for example on the outside of the application probe 42, to the application probe head 44 and is returned in an interior coaxial conduit to be introduced in the grip element 4 into the second return pressure hose 2' in order to flow back to the supply unit 40.

Considering the surgical instrument 30 shown here and, in particular, considering a standard cryosurgical instrument, the operating pressure of the application fluid in the pressure hose 2 and, in particular in the connecting region 10 (shown in FIG. 2 and described in greater detail below) is between 40 and 65 bar, whereby a safety limit of 130 bar should be prespecified. In doing so, it is an absolute requirement that the fluid-tightness and gas-tightness be 100% in the surgical environment. To this extent, special requirements exist for the connecting region 10 (see also FIG. 2) between the tubing set 3 and the pressure hoses 2, 2' respectively, and the grip element 4 of the handle 6.

Figure 2:
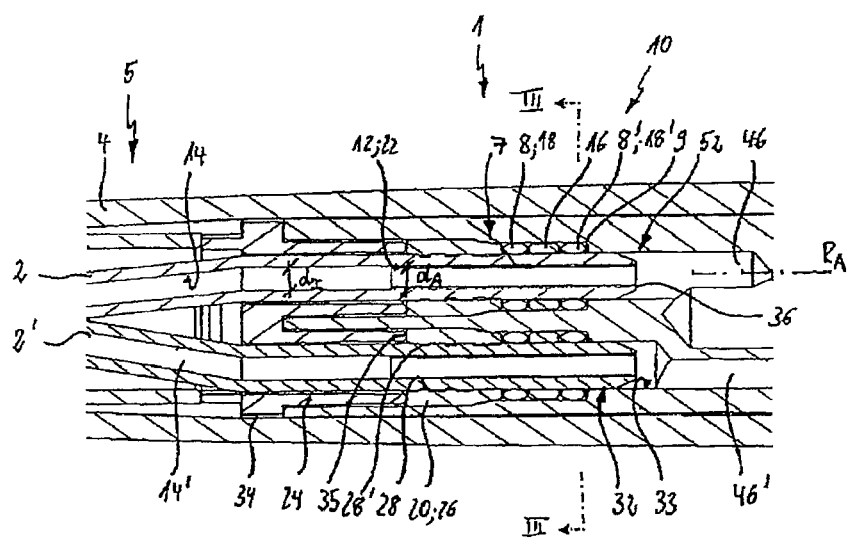
FIG. 2 is a view of a detail of a connecting region of a pressure hose and a grip element of the surgical instrument in accordance with FIG. 1.
Figure 3:
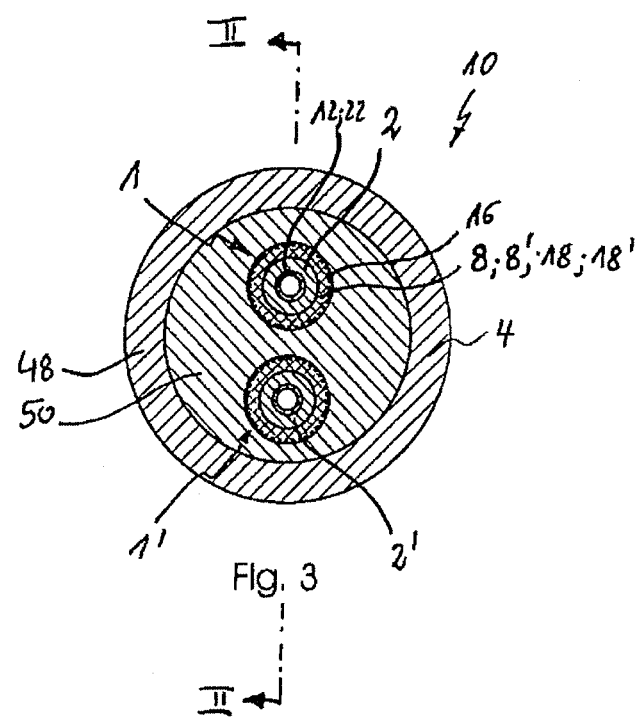
FIG. 3 is a cross-section through the connecting region of FIG. 2 along the section line of FIG. 2.

To ensure a safe connection of the pressure hoses 2, 2' with the grip element 4 of the handle 6 in this situation, the disclosed connecting device 1 or the disclosed handle have the design that is shown, in particular, in FIGS. 2 and 3.

FIG. 2 shows a longitudinal section through the connecting region 10 between the pressure hose 2 and the grip element 4 along the section line II of FIG. 1, and FIG. 3 shows a cross-section through the connecting region 10 in accordance with the section line of FIG. 2.

The two pressure hoses 2, 2' are attached in a sealing manner to the grip element 4, said two pressure hoses being inserted from the proximal end 5 of said grip element (see also FIG. 1). In doing so, the pressure hoses 2, 2' are arranged such that they are in fluid communication with continuing line elements 46, 46' to supply the application fluids supplied by the supply unit 40 (see FIG. 1) to the application probe 42.

Each pressure hose 2, 2' is attached to the grip element 4 via an embodiment of the connecting device 1.

The connecting device 1 comprises two sealing elements 8, 8' having the form of O-rings 18, 18' in a sealing element receptacle 9. The sealing element receptacle 9 is a part of a receiving region 7 that is provided in the grip element 4 such that it enables the insertion of the pressure hose 2 and additional components that will be described in detail below.

In an axial direction $R_A$ of the (attached) pressure hose 2, a spacer element 16 configured as a stand-alone component is interposed between the two sealing elements 8, 8' or O-rings 18, 18', said spacer element being embodied here as a spacer element ring and uncoupling the two spacer sealing elements 8, 8' or O-rings 18, 18' from each other.

FIG. 3 shows this spacer element 16 in dashed lines. As is also shown in FIG. 3, the grip element 4 consists of an outer grip element sheath 48 and an inner grip element core 50 in which the connecting device 1 is provided and which, in addition, contains the continuing line elements 46, 46'.

In accordance with the embodiments of the invention, each pressure hose 2, 2' has in its interior 14, 14' a support element 12 configured as a support bushing 22 that is inserted into the interior 14, 14' of the pressure hose 2, 2' such that it is fixed in place in a snugly fitting manner and, in particular, slightly expands the pressure hose 2, 2'. The support bushing 22 is configured such that it has an outside diameter $d_A$ that is complementary to the inside diameter $d_1$ of the pressure hose 2 and that is slightly greater so that the support element 12 in the interior 14 of the pressure hose 2 expands said pressure hose.

In the illustrated embodiment, an insertion element 36 is provided on the free distal end 52 of the pressure hose 2 and the support element 12, said insertion element enabling the easy insertion of the pressure hose 2 and of the support element 12 into the receiving region 7 of the grip element 4 or the interior core 50. In this embodiment, the insertion element 36 is represented by the chamfered corner regions of the free distal end 52 of the pressure hose 2.

For the sealing connection of the pressure hose 2 with the grip element 4, the sealing elements 8 configured as O-rings 18 are slipped over the pressure hose 2 and are configured such that they, after the insertion of the pressure hose 2 into the receiving region 7 of the grip element 4, ensure a sealing connection between the outside 32 of the pressure hose 2 and the inside 33 of the grip element 4 in connecting region 10 or in receiving region 7. Due to the arrangement of the sealing elements 8 and their radial compression, only minimal deformation will occur so that, even at higher temperatures, a lasting sealing connection remains ensured.

To secure the pressure hose 2 in position, in particular in axial direction $R_A$, a holding element 20 in the form of a crimp ring 26 is provided on the outside 32 of each pressure hose 2 and is pressure-fitted or similarly fixed in place on the outside 32. To improve this fixation, the holding element 20 comprises fixation extensions 28,28' that project in the direction of the interior 14 of the pressure hose 2.

This holding element 20 or the crimp ring 26 is in operative connection with an abutment element 24, the abutment element being attached to the grip element 4 via fastening means 34 such that said fastening means prevents the pressure hose 2 from being pulled out of the receiving region 7 of the grip element 4 in the axial direction $R_A$. To accomplish this, a support extension 35 of the abutment element 24 directly abuts against the holding element 20 or the crimp ring 26 so that tensile forces introduced by the pressure hose 2 into the holding element 20 are introduced, via the support extension 35 and the fastening means 34, into the grip element 4.

The fastening means 34 used for connecting an abutment element 24 with a grip element 4, may be, for example, a screw connecting means, a locking means, etc., as is known in the art.

From the above description should be appreciated that the embodiments of the invention can also be used for the connection between a pressure hose and a connector, which can be plugged into the supply unit (or a grip element) that are also into an extension coupling.

The invention claimed is:

1. A device for the sealing connection of a flexible pressure hose with a grip element of a surgical instrument or a connector of a surgical instrument, said device comprising:
    at least one sealing element that, in an assembled state, is interposed between the grip element and the flexible pressure hose in a connecting region so as to create a seal between the flexible pressure hose and a sealing element receptacle of the grip element;
    a support element being arranged in an end region of the flexible pressure hose such that the end region of the flexible pressure hose is stiffened and arranged as a stiff plug member that is plugged into the sealing element receptacle of the grip element and such that the sealing element is clamped, or can be clamped, between the support element and the stiff plug member on one side and the grip element on the other side, wherein the support element comprises a support bushing that has an outside diameter that is complementary to an inside diameter of the flexible pressure hose, wherein the outside diameter of the support bushing is slightly greater than the inside diameter of the flexible pressure hose so that the support element in the interior of the flexible pressure hose expands and stiffens said flexible pressure hose; and
    a crimp ring fixedly crimped around the stiff plug member and arranged between an abutment element of the grip element and the sealing element receptacle to prevent axial movement of the flexible pressure hose in the connecting region;
    wherein the flexible pressure hose is connected to a cryosurgical fluid supply;
    wherein said grip element is connected to a cryosurgical probe;
    wherein the connection between the flexible pressure hose and the grip element can withstand an operating pressure between about 40 bar and 65 bar; and
    wherein the connection is fluid-tight and gas-tight for sealing the connection within a surgical environment.

2. The device of claim 1, wherein the sealing element comprises at least one O-ring circumscribing the flexible pressure hose and the support element in the assembled state.

3. The device of claim 2, wherein an insertion element is arranged or configured on a free distal end of at least one of the flexible pressure hose and the support element such that said insertion element assists the insertion of the flexible pressure hose together with the support element into an interior of the O-ring.

4. The device of claim 1, wherein the sealing element comprises an enveloping element circumscribing the flexible pressure hose and the support element in the assembled state.

5. The device of claim 4, wherein an insertion element is arranged or configured on a free distal end of at least one of the flexible pressure hose and the support element such that said insertion element assists the insertion of the flexible pressure hose together with the support element into an interior of the enveloping element.

6. The device of claim 1, wherein the sealing element comprises at least two O-rings circumscribing the flexible pressure hose and the support element, said O-rings being uncoupled from each other by at least one spacer element.

7. The device of claim 1, wherein the sealing element comprises at least two enveloping elements circumscribing the flexible pressure hose and the support element, said enveloping elements being uncoupled from each other by at least one spacer element.

8. The device of claim 1, wherein the crimp ring has at least one fixation extension that, in an assembled state, projects from the outside of the flexible pressure hose in the direction of the interior of the flexible pressure hose.

9. The device of claim 1, wherein the abutment element comprises at least one fastening means that can be used to bring said abutment element into a specifically releasable locking or supporting engagement with at least one of the grip element and with the holding element crimp ring.

10. The device of claim 1, wherein sealing element is arranged between the crimp ring and the sealing element receptacle.

11. The device of claim 1, wherein the interface between the sealing element receptacle and the sealing element prevents the stiff plug member from being advanced further into the grip element.

12. The device of claim 1, wherein the interface between the crimp ring and the abutment element prevents the stiff plug member from being removed from the grip element.

13. A handle for a surgical instrument comprising:
    a grip element connected to a cryosurgical instrument; and
    a device for sealing a connection of at least one flexible pressure hose with the grip element, said device comprising:
    at least one sealing element that, in an assembled state, is interposed between the grip element and the flexible pressure hose in a connecting region so as to create a seal between the flexible pressure hose and a sealing element receptacle of the grip element; and
    a support element being arranged in the connecting region in an end region of the at least one flexible pressure hose such that the end region of the at least one flexible pressure hose is stiffened and arranged as a stiff plug member that is plugged into the sealing element receptacle of the grip element and such that the sealing element is clamped, or can be clamped, between the support element and the stiff plug member on one side and the grip element on the other side, wherein the support element comprises a support bushing that has an outside diameter that is complementary to an inside diameter of the at least one flexible pressure hose, wherein the outside diameter of the support bushing is slightly greater than the inside diameter of the at least one flexible pressure hose so that the support element in the interior of the at least one flexible pressure hose expands and stiffens said at least one flexible pressure hose; and a crimp ring fixedly crimped around the stiff plug member and arranged between an abutment element of the grip element and the sealing element receptacle to prevent axial movement of the at least one flexible pressure hose in the connecting region;

wherein the flexible pressure hose is connected to a cryosurgical fluid supply;

wherein the connection between the flexible pressure hose and the grip element can withstand an operating pressure between about 40 bar and 65 bar; and wherein the connection is fluid-tight and gas-tight for sealing the connection within a surgical environment.

14. The handle of claim 13, wherein the handle is for a cryosurgical instrument.

15. The handle of claim 13, wherein the sealing element comprises at least one O-ring or an enveloping element circumscribing the at least one flexible pressure hose and the support element in the assembled state.

16. The handle of claim 13, wherein the sealing element comprises at least two O-rings or enveloping elements circumscribing the at least one flexible pressure hose and the support element, said O-rings being uncoupled from each other by at least one spacer element.

17. The handle of claim 13, wherein sealing element is arranged between the crimp ring and the sealing element receptacle.

18. The handle of claim 13, wherein the interface between the sealing element receptacle and the sealing element prevents the stiff plug member from being advanced further into the grip element.

19. The handle of claim 13, wherein the interface between the crimp ring and the abutment element prevents the stiff plug member from being removed from the grip element.

* * * * *